United States Patent
Pocock et al.

(10) Patent No.: US 7,779,839 B2
(45) Date of Patent: Aug. 24, 2010

(54) FLUID PRODUCT DISPENSING DEVICE

(75) Inventors: Andrew Pocock, Royston (GB); Stuart Kay, Melbourn (GB); Paul Greenhalgh, Newport Pagnell (GB); Wayne O'Hara, Cambridge (GB); Xavier Donnette, Plaisir (FR)

(73) Assignee: Valois S.A.S, Le Neubourg (FR)

( * ) Notice: Subject to any disclaimer, the term of this patent is extended or adjusted under 35 U.S.C. 154(b) by 605 days.

(21) Appl. No.: 11/795,864

(22) PCT Filed: Jan. 25, 2006

(86) PCT No.: PCT/FR2006/050054

§ 371 (c)(1),
(2), (4) Date: Jul. 24, 2007

(87) PCT Pub. No.: WO2006/079746

PCT Pub. Date: Aug. 3, 2006

(65) Prior Publication Data

US 2008/0099015 A1     May 1, 2008

(30) Foreign Application Priority Data

Jan. 25, 2005     (FR) .................................. 05 50210

(51) Int. Cl.
*A61M 11/00*     (2006.01)

(52) U.S. Cl. .............................. 128/203.21; 128/203.15

(58) Field of Classification Search ............ 128/203.21, 128/203.15, 203.12, 205.21, 203.22, 203.23
See application file for complete search history.

(56) References Cited

U.S. PATENT DOCUMENTS

| 6,427,688 | B1 * | 8/2002 | Ligotke et al. | ......... 128/203.15 |
| 6,543,448 | B1 | 4/2003 | Smith et al. | |
| 6,880,555 | B1 * | 4/2005 | Brunnberg et al. | ..... 128/203.12 |
| 7,275,537 | B2 * | 10/2007 | Nelson et al. | .......... 128/203.15 |
| 7,322,354 | B2 * | 1/2008 | Young et al. | ........... 128/203.15 |
| 2002/0032409 | A1 | 3/2002 | Ritsche | |

FOREIGN PATENT DOCUMENTS

| WO | WO 98/34660 A1 | 8/1998 |
| WO | WO 01/26720 A1 | 4/2001 |
| WO | WO 2004/067069 A2 | 8/2004 |

* cited by examiner

*Primary Examiner*—Steven O Douglas
(74) *Attorney, Agent, or Firm*—Sughrue Mion, PLLC

(57) ABSTRACT

A fluid dispenser device including at least one individual reservoir (21) containing a single dose of fluid, opening means (40) being provided for opening an individual reservoir (21) each time the device is actuated, said opening means (40) comprising perforator and/or cutter means (41) and movable support means (50), said movable support means (50) being adapted to displace an individual reservoir (21) against said perforator and/or cutter means (41) on each actuation.

27 Claims, 11 Drawing Sheets

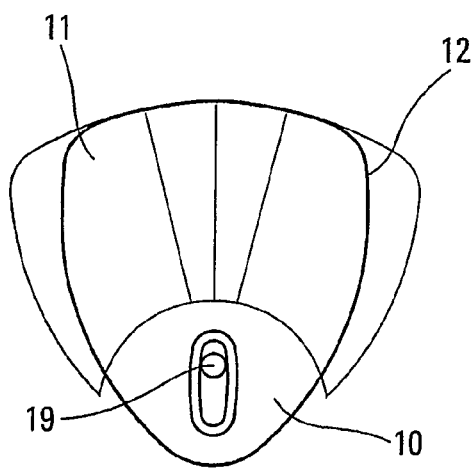
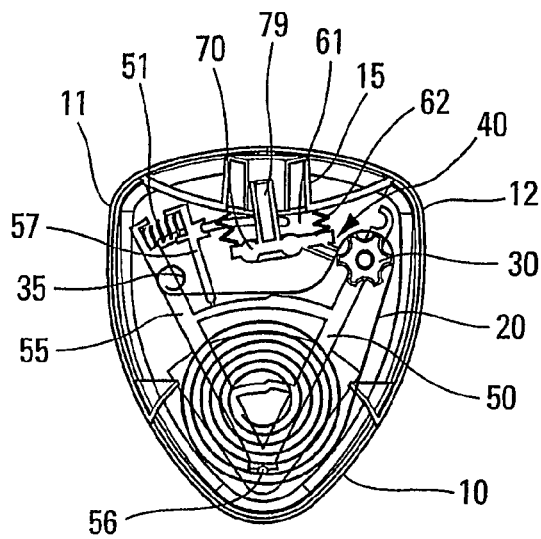
Fig. 5a    Fig. 5b
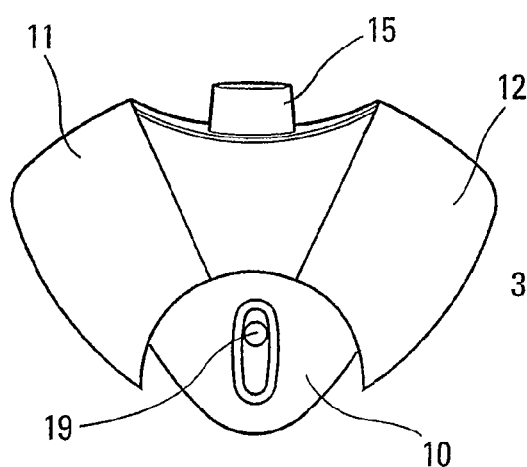
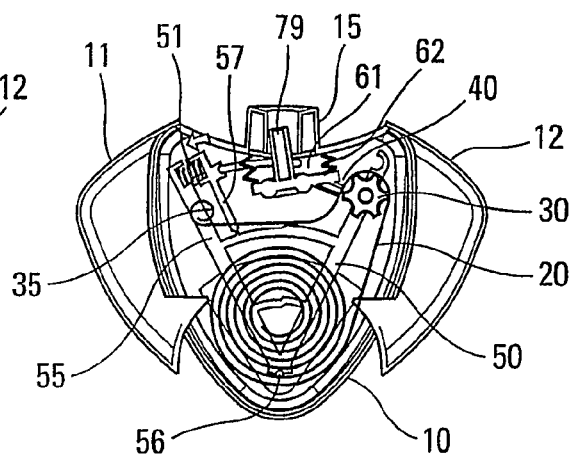
Fig. 6a    Fig. 6b

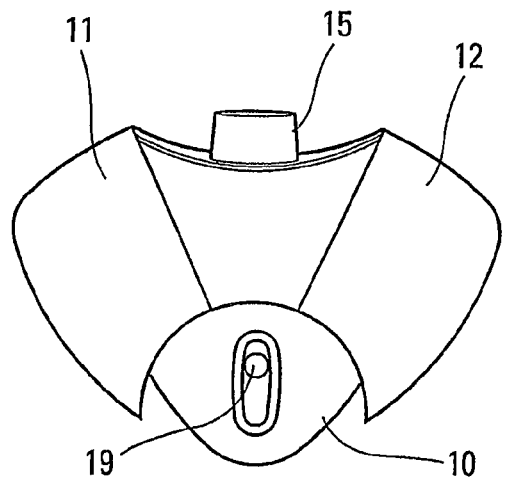
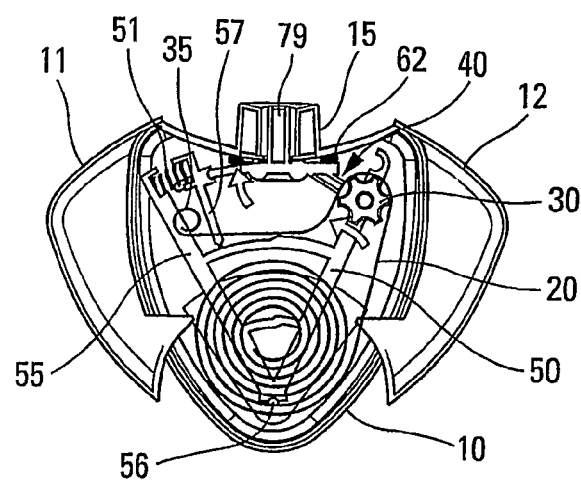
Fig. 7a  Fig. 7b
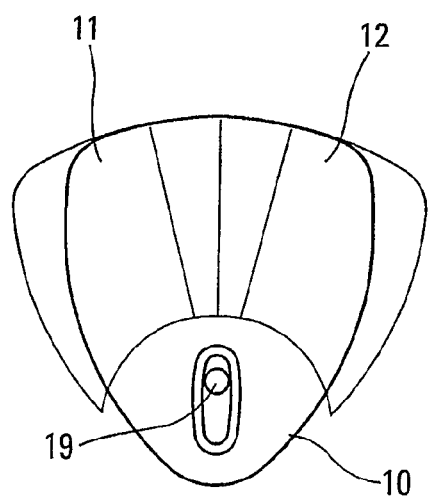
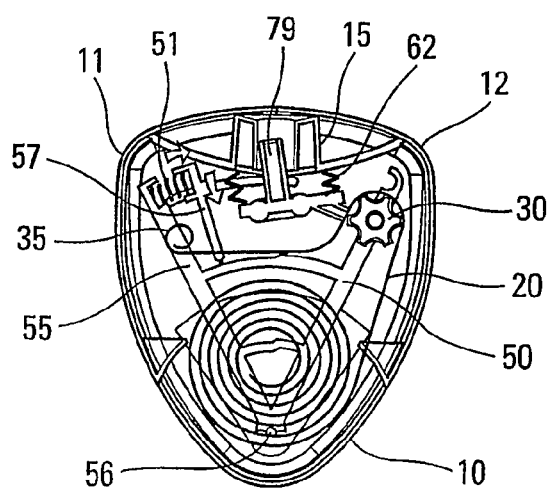
Fig. 8a  Fig. 8b

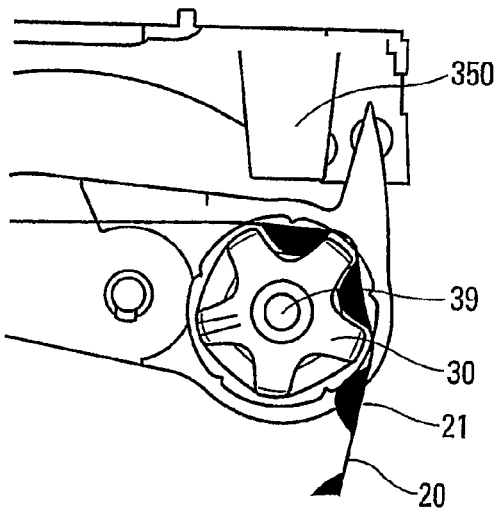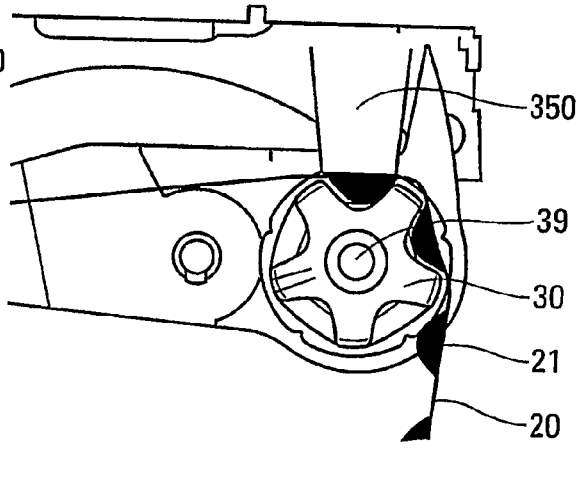
Fig. 35   Fig. 36
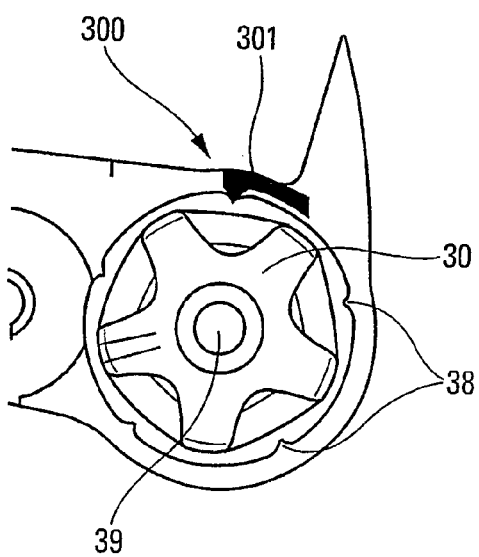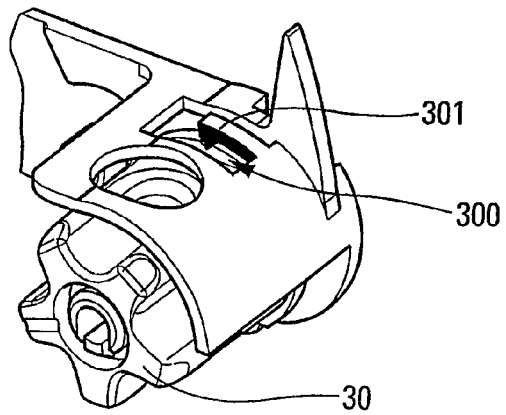
Fig. 37   Fig. 38

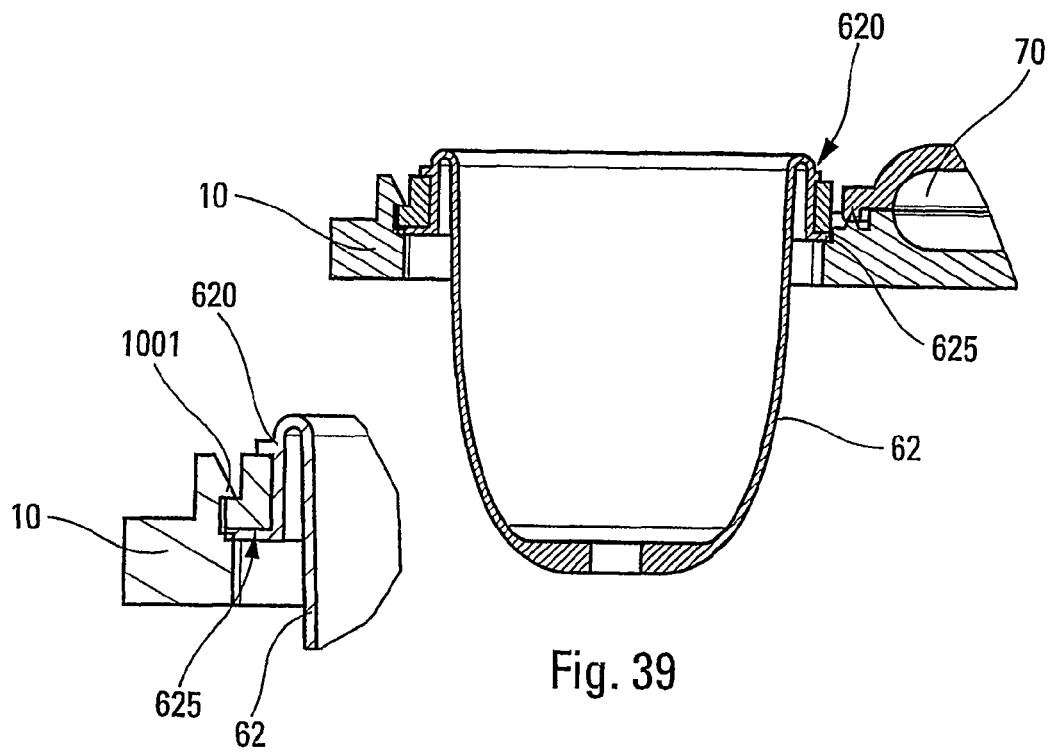
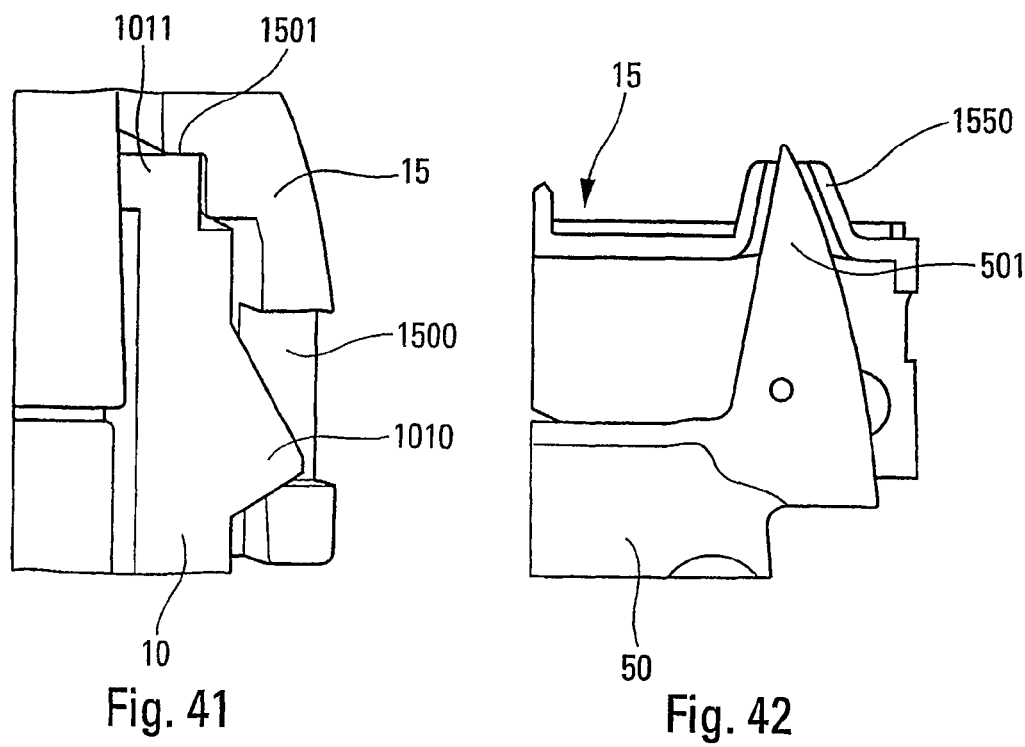

FLUID PRODUCT DISPENSING DEVICE

The present invention relates to a fluid dispenser device, and more particularly to a dry-powder inhaler.

Dry-powder inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Another type of inhaler consists in packaging the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. Inhalers including individual reservoirs, such as capsules, that are loaded into the inhaler just before said reservoir is used are also described in the prior art. The advantage of such devices is that it is not necessary to store all of the doses inside the appliance, such that said appliance can be compact. Obviously however, the inhaler is more difficult to use, since the user is obliged to load a capsule into the inhaler before each use. All existing types of inhalers, including those described above, present both advantages and drawbacks associated with their structures and with their types of operation. Thus, with certain inhalers, there is the problem of accuracy and of reproducibility for the dose on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. Once again, that can create drawbacks, in particular in that type of device, the dose is generally loaded into an expulsion duct before inhalation, then expulsion is synchronized with inhalation. That means that if the user drops, shakes, or manipulates the inhaler in an undesirable or inappropriate manner between the moment when the user loads the dose (either from a multidose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the previous dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. With regard to opening the individual reservoirs, it has been proposed to peel off or to unstick the closure layer. That presents the drawback of difficulty in controlling the forces to be applied in order to guarantee complete opening, without running the risk of opening the next reservoir, particularly if the opening means need to be actuated by inhalation. In a variant, it has been proposed to perforate the closure layer or wall. That presents the drawback that the cut wall-portions risk retaining a fraction of the dose inside the reservoir, so that metering accuracy and reproducibility are therefore not guaranteed.

An object of the present invention is to provide a fluid dispenser device, in particular a dry-powder inhaler, that does not have the above-mentioned drawbacks.

In particular, an object of the present invention is to provide such an inhaler that is simple and inexpensive to manufacture and to assemble, that is reliable in use, guaranteeing metering accuracy and metering reproducibility on each actuation, providing an optimum yield with regard to the effectiveness of the treatment, by making it possible to dispense a substantial fraction of the dose to the zones to be treated, in particular the lungs, avoiding, in safe and effective manner, any risk of overdosing, and that is as compact as possible, while guaranteeing sealing and absolute integrity of all of the doses up to their expulsion.

The present invention therefore provides a fluid dispenser device including at least one individual reservoir containing a single dose of fluid, such as powder, opening means being provided for opening an individual reservoir each time the device is actuated, said opening means comprising perforator and/or cutter means and movable support means, said movable support means being adapted to displace an individual reservoir against said perforator and/or cutter means on each actuation.

Advantageously, said movable support means are displaceable between a non-dispensing position and a dispensing position, said movable support means being urged towards their dispensing position by resilient means, such as a spring or a spring blade, and being held in their non-dispensing position by blocking means.

Advantageously, said blocking means are released by the user inhaling.

Advantageously, said resilient means are deformable between a rest position, in which they do not urge the movable support means towards their dispensing position, and a stressed position, in which they urge said movable support means towards their dispensing position, said resilient means being deformed manually into their stressed position before the user inhales.

Advantageously, said device comprises a body and a cap that is movable between a closed position and an open position, opening the cap deforming the resilient means into their stressed position.

Advantageously, the movable support means are displaced in a curve between the non-dispensing and dispensing positions.

Advantageously, said blocking means comprise a first element that is movable between a non-actuated position and an actuated position, said first element being secured to said movable support means, and a second element that is movable between a blocking position and an unblocking position, said second element being displaced towards its unblocking position while the user is inhaling.

Advantageously, said second element is displaceable in turning.

Advantageously, said second element co-operates with a displaceable and/or deformable unit that is adapted to be displaced and/or deformed during inhalation.

Advantageously, said displaceable and/or deformable unit comprises a deformable air-chamber that is connected to an inhaler endpiece.

Advantageously, said deformable air-chamber comprises a deformable membrane, such as a bellows.

Advantageously, said chamber contracts during inhalation, causing the second element of said blocking means to be displaced towards its unblocking position.

Advantageously, a dispenser chamber is provided for receiving the dose of fluid contained in a reservoir after said reservoir has been opened, said dispenser chamber being connected firstly to said opening means, and secondly to a dispenser orifice that is connected to an inhaler endpiece.

Advantageously, said dispenser chamber contains at least one movable bead.

Advantageously, said dispenser chamber is secured to said displaceable and/or deformable unit, such that said dispenser chamber is displaced during inhalation.

In a variant embodiment, said opening means do not move while the reservoir is being opened.

In another variant embodiment, said opening means move while the reservoir is being opened.

Advantageously, said movable support means support a guide wheel.

Advantageously, the reservoirs are made in the form of an elongate strip comprising a plurality of individual reservoirs disposed one behind another.

Advantageously, the guide wheel includes at least one recess that is adapted to receive and to guide a reservoir.

Advantageously, said guide wheel is firstly turnable about its central pin so as to cause the elongate strip to advance, and secondly displaceable, together with the movable support means, towards a dispensing position, so as to bring a reservoir into contact with the reservoir opening means.

Advantageously, the guide wheel is turned manually by the user, whereas its displacement towards the dispensing position takes place automatically by the user inhaling.

Advantageously, said guide wheel co-operates with rotary positioning means that are adapted to determine the rotary position of said guide wheel.

Advantageously, said positioning means comprise a projection or finger that co-operates with notches provided on the guide wheel.

Advantageously, in the dispensing position, the guide wheel co-operates with abutment means that are adapted to determine the dispensing position of said guide wheel after inhalation.

Advantageously, said abutment means comprise a lug that is adapted to co-operate with at least one plane surface of said guide wheel in the dispensing position.

Advantageously, said opening means comprise perforator and/or cutter means that are adapted to cut a closure wall of the reservoir in such a manner that the cut portion(s) does/do not obstruct the opening(s) that is/are formed.

Advantageously, the dispenser device includes a dose indicator for indicating to the user the number of doses that have been dispensed or that remain to be dispensed.

These characteristics and advantages and others of the present invention appear more clearly from the following detailed description of several embodiments and variants thereof, given by way of non-limiting example, and with reference to the accompanying drawings, in which.

Figure 1:
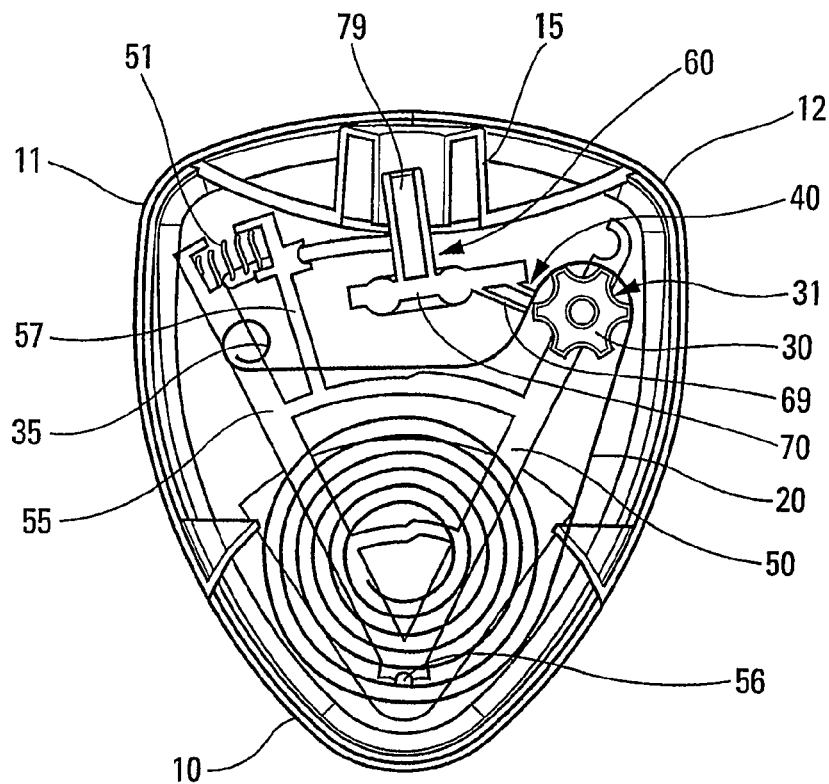
FIG. 1 is a diagrammatic section view of a dispenser device constituting a first embodiment.
Figure 2A:
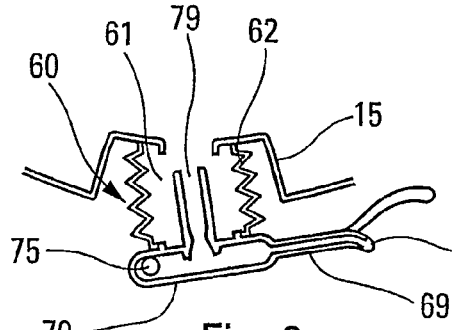
FIGS. 2a and 2b are views of a detail of an inhalation trigger system constituting an advantageous embodiment, respectively without and during inhalation.
Figure 2B:
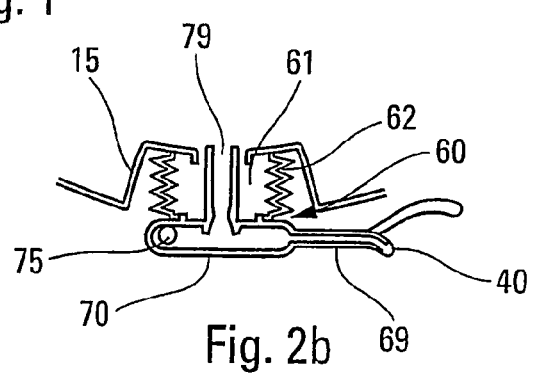
Figure 9:
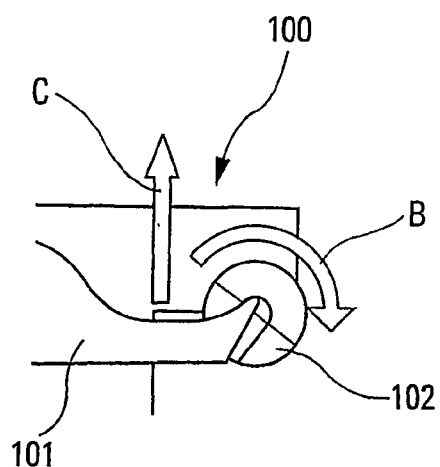
Figure 10:
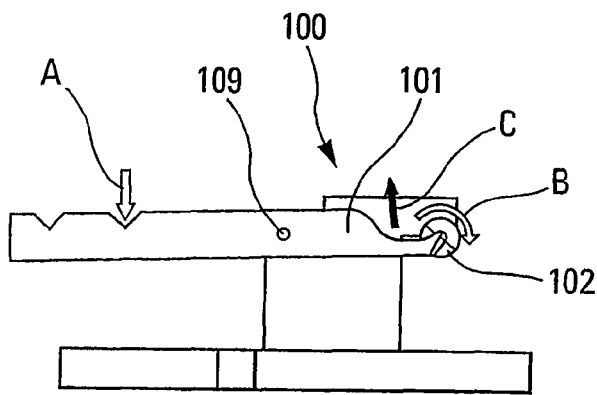
Figure 11:
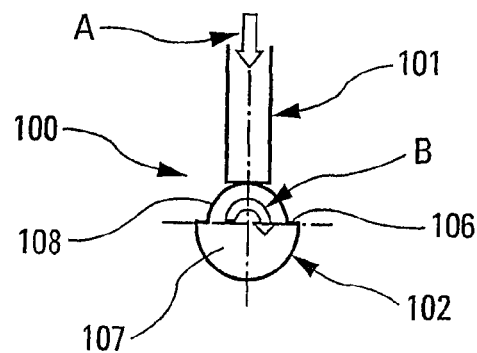
Figure 12:
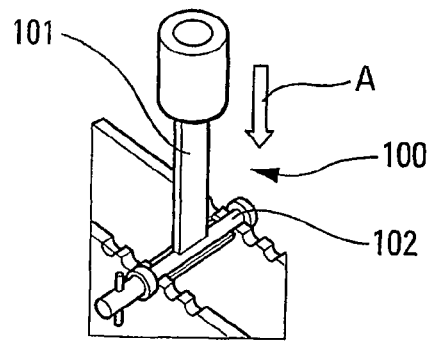
Figure 13:
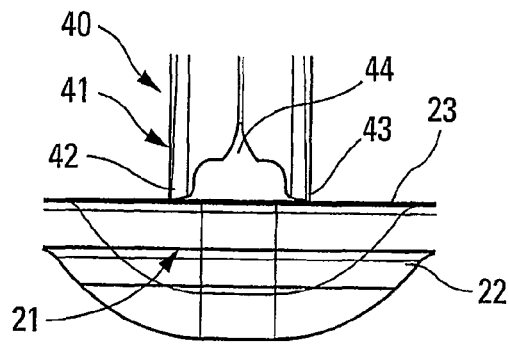
Figure 14:
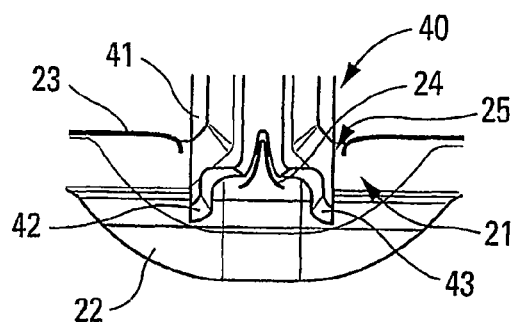
Figure 15:
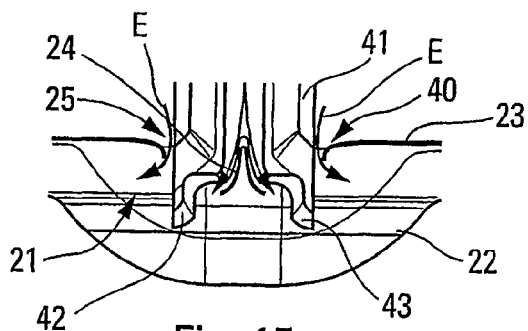
Figure 17:
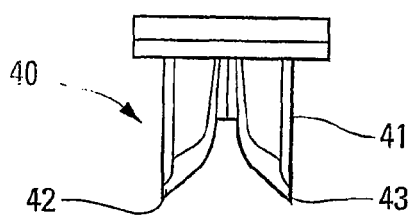
Figure 18:
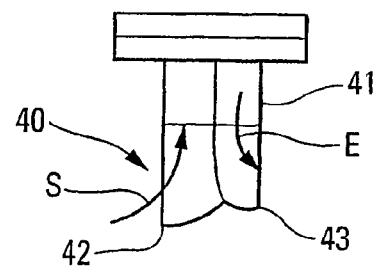
Figure 19:
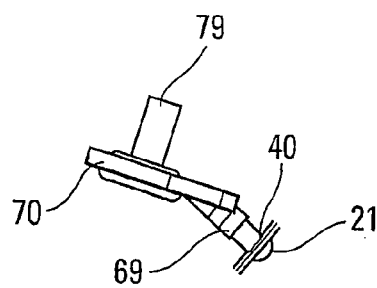
Figure 20:
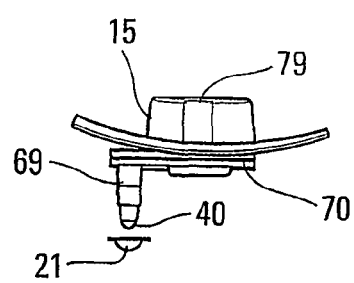
Figure 21:
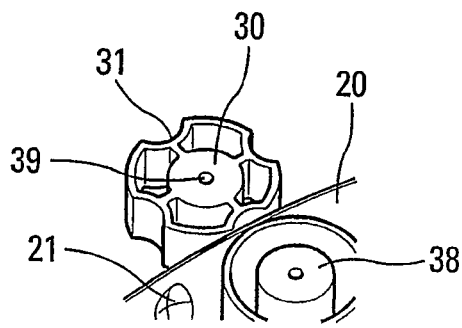
Figure 22:
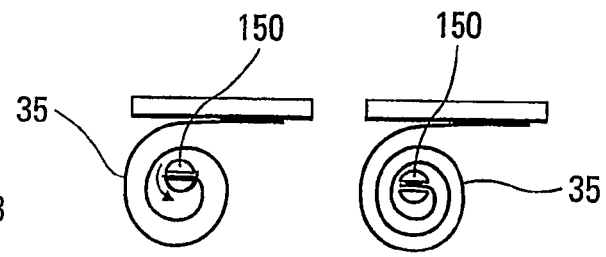
Figure 23:
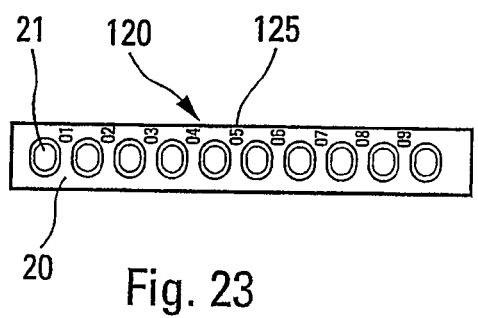
Figure 24:
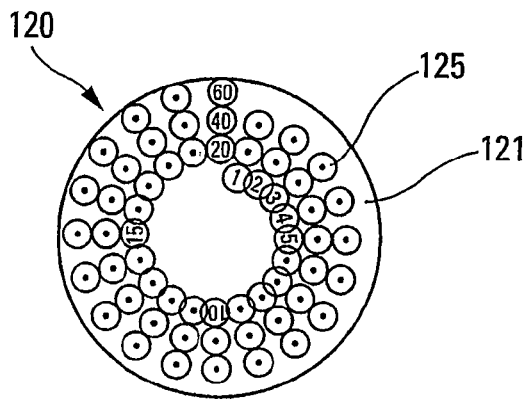
Figure 25:
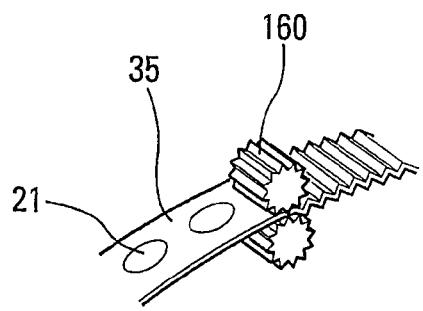
Figure 26:
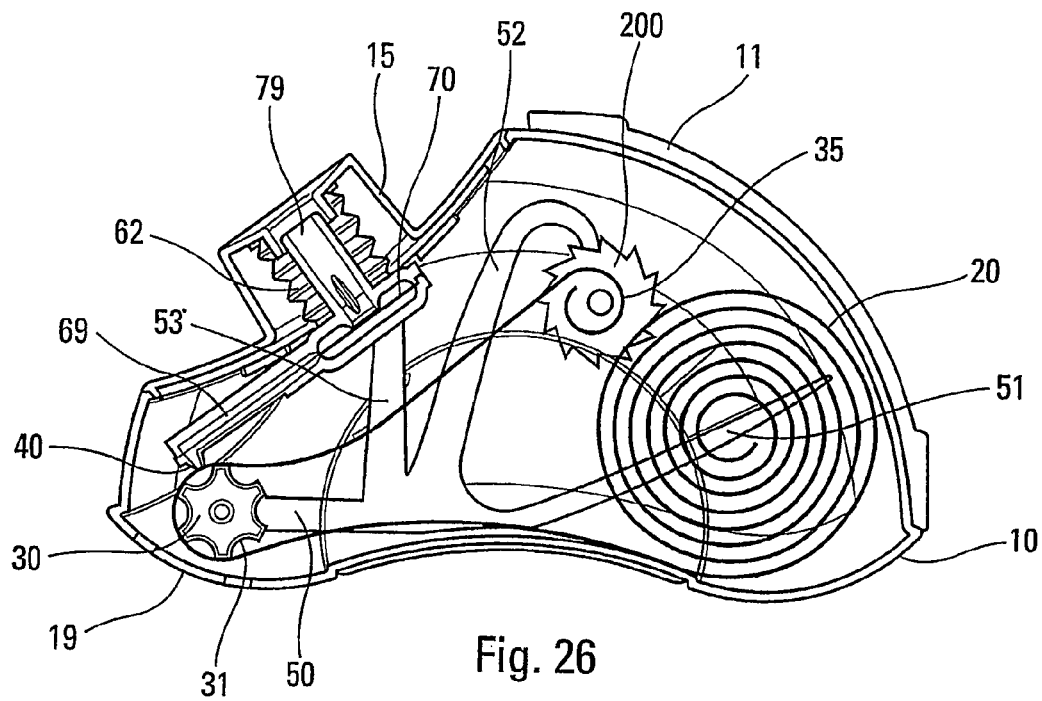
Figure 27:
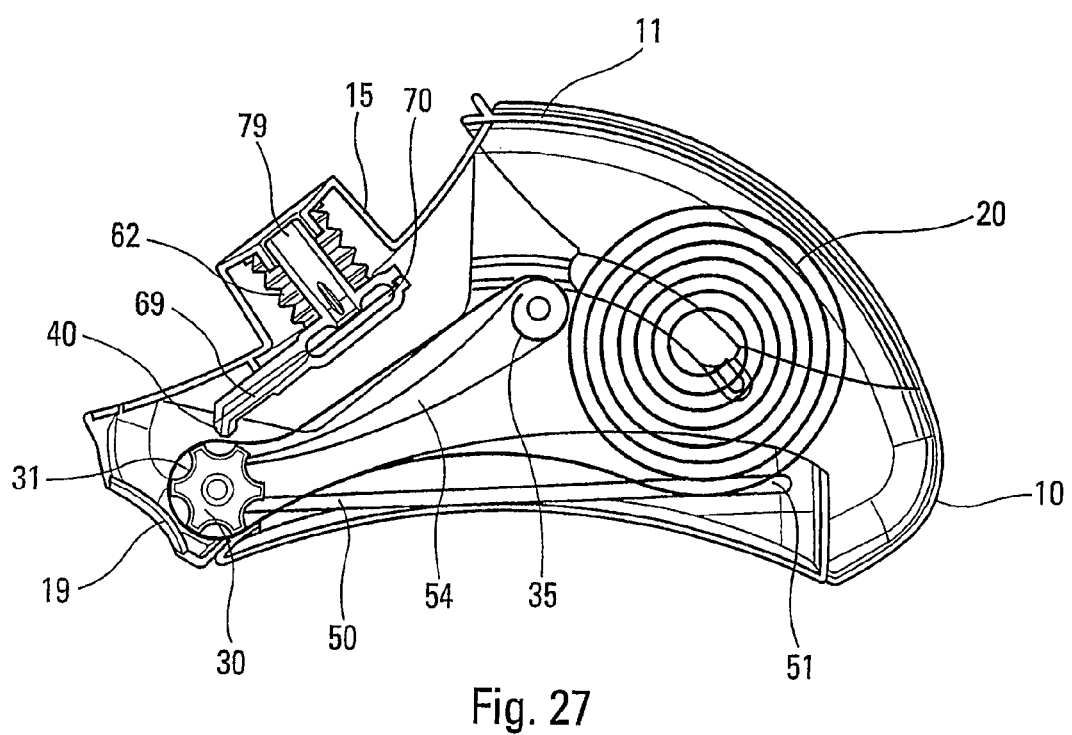
Figure 28:
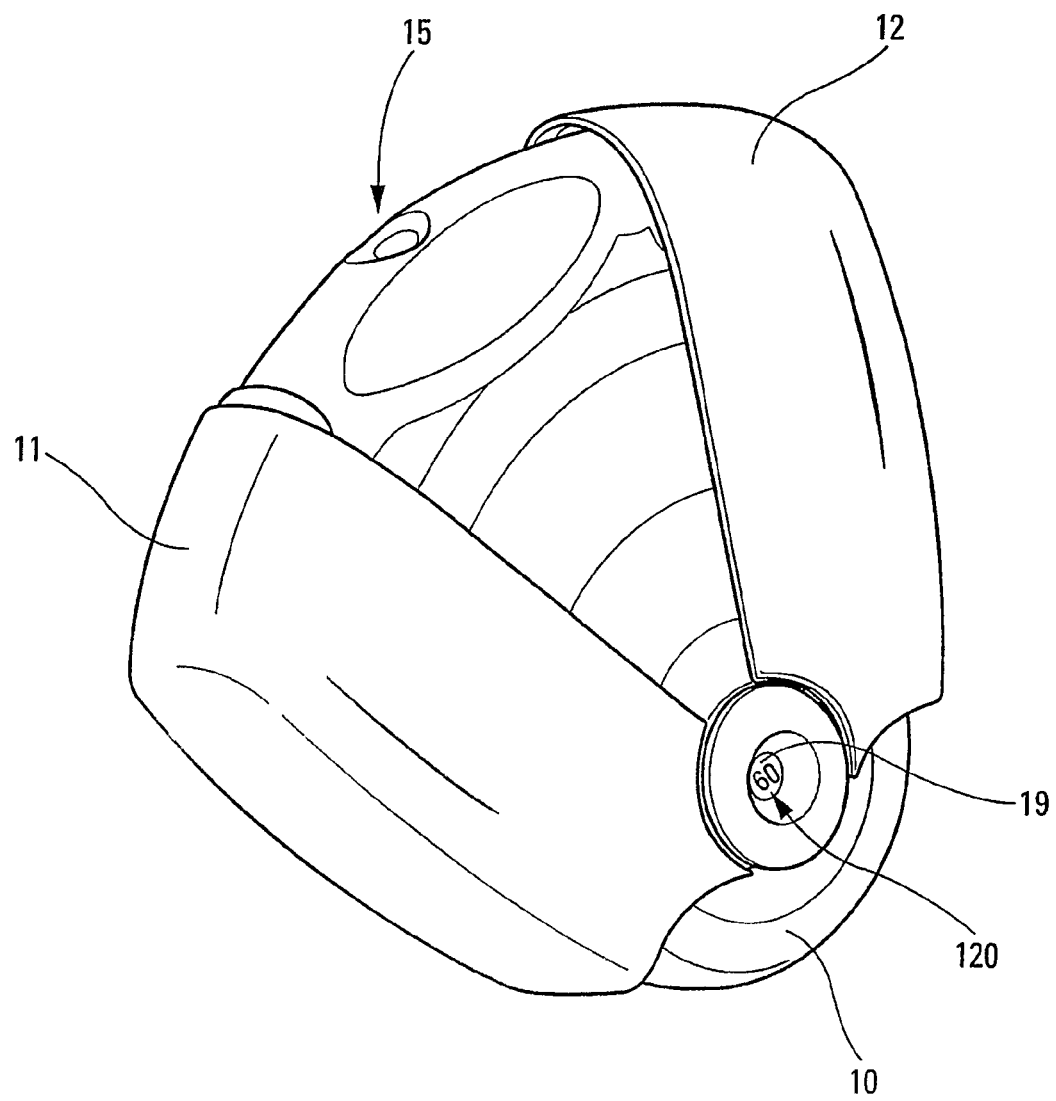
Figure 29:
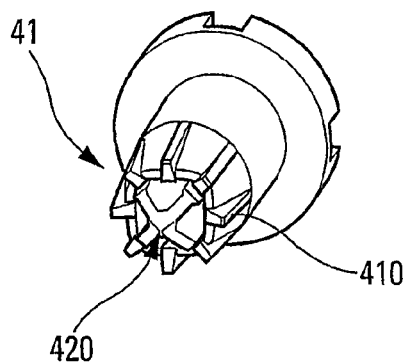
Figure 30:
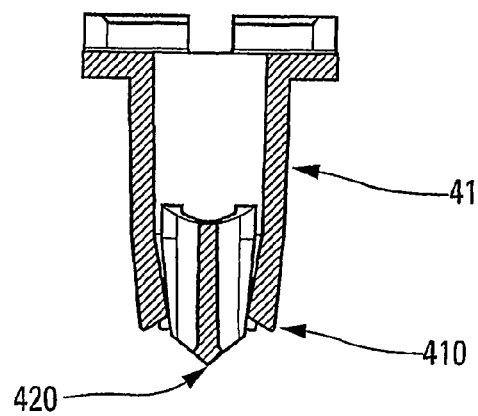
Figure 31:
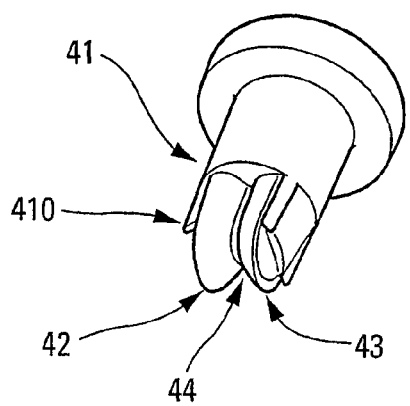
Figure 32:
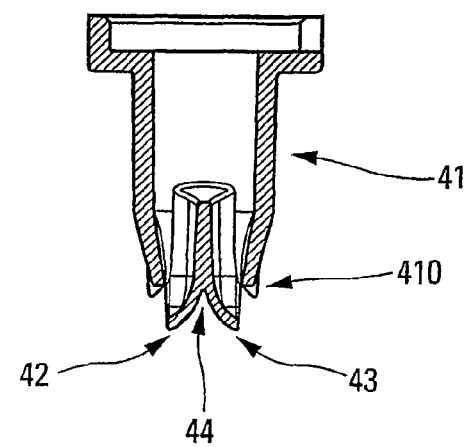
Figure 33:
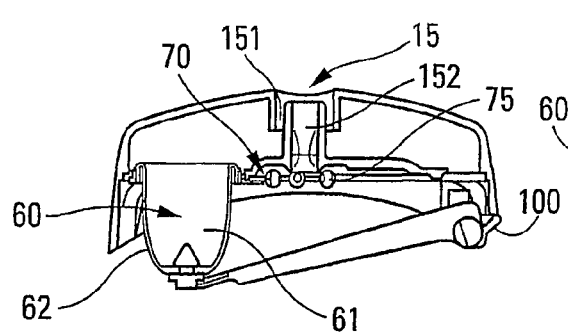
Figure 34:
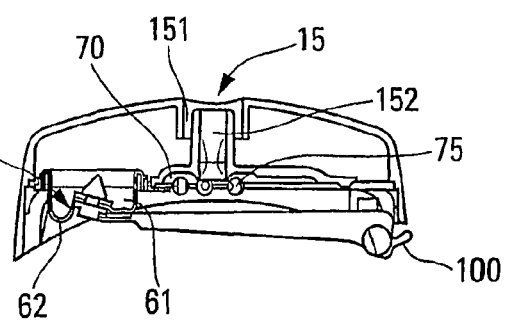

FIGS. 5a to 8b show a utilization sequence of the FIG. 1 device, respectively showing an external view and an internal view of the device for the respective steps of rest (FIGS. 5a and 5b), of stressing or opening the device (FIGS. 6a and 6b), of inhaling (FIGS. 7a and 7b), and of end of use or closure of the device (FIGS. 8a and 8b);

FIGS. 9 and 10 are diagrams showing blocking means constituting a first variant embodiment;

FIGS. 11 and 12 show another variant embodiment of the blocking means;

FIGS. 13 to 16 are diagrams showing opening means constituting an advantageous embodiment, respectively before a reservoir is opened, after it has been opened, while air is flowing into the reservoir, and while air and powder are flowing out of the reservoir;

FIG. 17 shows advantageous perforator and/or cutter means;

FIG. 18 shows a variant embodiment of the perforator and/or cutter means;

FIGS. 19 and 20 show two variant embodiments of the opening means, the FIG. 19 reservoir being in its open position;

FIG. 21 is a diagram showing, in detail, an advantageous variant of the movable support means;

FIG. 22 is a diagram showing, in detail, receiver means for receiving a used strip;

FIGS. 23 and 24 are diagrams showing, in detail, two variants of dose-indicator means;

FIG. 25 is a diagram showing, in detail, flattener means for flattening empty reservoirs;

FIGS. 26 and 27 are views similar to FIG. 1 and respectively show two other embodiments of the dispenser device;

FIG. 28 is a diagrammatic perspective view of still another embodiment of the invention;

FIG. 29 is a diagrammatic perspective view of another variant embodiment of the perforator and/or cutter means;

FIG. 30 is a diagrammatic section view of the FIG. 29 perforator and/or cutter means;

FIG. 31 is a view similar to the view in FIG. 29, showing still another variant embodiment of the perforator and/or cutter means;

FIG. 32 is a diagrammatic section view of the FIG. 31 perforator and/or cutter means;

FIG. 33 is a fragmentary and diagrammatic section view of still another embodiment of the inhalation trigger system, in its pre-inhalation position;

FIG. 34 is a view similar to the view in FIG. 33, post inhalation;

FIG. 35 is a diagrammatic section view of the movable support means in their non-dispensing position;

FIG. 36 is a view similar to the view in FIG. 35, in the dispensing position;

FIGS. 37 and 38 are diagrammatic views respectively in section and in perspective of the rotary positioning means that co-operate with the movable support means;

FIG. 39 is a diagrammatic section view of a variant embodiment of the diaphragm in FIGS. 33 and 34;

FIG. 40 is a view of a detail of the FIG. 39 diaphragm;

FIG. 41 is a diagrammatic perspective view showing the fastening of the mouthpiece on the body, constituting a particular embodiment; and FIG. 42 is a diagrammatic section view showing an example of control means for controlling the inhalation flow, in the inhalation position.

FIGS. 1 to 8b show a first embodiment of a dry-powder inhaler. The inhaler comprises a central body 10 on which there are slidably mounted two lateral portions 11, 12 that form a cap when the device is closed and that are adapted to be moved apart in order to open the device and thus stress the device as described below. The body 10 can be approximately rounded in shape, as shown in the figures, but it could be of any other appropriate shape. The body 10 includes a mouthpiece or inhaler endpiece 15 through which the user inhales while the device is being actuated. The two cap-forming lateral portions 11, 12 can be opened by pivoting about a common pivot axis as shown in the figures, but any other opening means can be envisaged for opening the device. Alternatively, it is possible to provide only one cap element 11 that is movable relative to the body 10, as shown in FIGS. 26 and 27.

The body advantageously includes a window 19 through which the count of the doses that have been dispensed or that remain to be dispensed can be displayed in visible manner for the user. The window 19 can advantageously be provided on or close to the pivot axis of the cap-forming lateral portions 11, 12. Inside the body 10 there is provided a strip 20 of individual reservoirs 21, also known as blisters, said strip preferably being an elongate strip 20 on which the blisters 21 are disposed one behind another, in manner known per se. The blisters 21 are not shown in the overall views in FIGS. 1, 5b, 6b, 7b, 8b, 26, and 27, so as not to clutter the drawings for the purpose of clarity, but they are visible in FIGS. 13 to 16 and 21 and 23. The blister strip 20 is advantageously constituted by a base layer or wall 22 that forms the cavities 21 receiving the doses of powder, and by a closure layer or wall 23 that covers each of said blisters 21 in sealed manner. The blister strip 20 can be rolled-up inside the body 10, and drive means 30 for driving the strip are provided for progressively unrolling the blister strip and for bringing a respective blister or individual reservoir 21 into a dispensing position each time the device is actuated. When an individual reservoir 21 has been emptied by inhalation, the strip portion 35 that includes said empty reservoirs is advantageously adapted to be rolled-up at another location of said body 10, as described in greater detail below.

In a first aspect of the inhaler, reservoir opening means 40 are provided in, or secured to, the body 10, the opening means 40 comprising perforator and/or cutter means 41 for perforating or cutting the closure layer of the blisters. Movable support means 50 are also provided in the device and are adapted to support a given reservoir that is to be opened during the next inhalation. The movable support means 50 are adapted to displace the reservoir to be emptied against said perforator and/or cutter means 41 of the device during actuation. Advantageously, the movable support means 50 are urged by a resilient element 51, such as a spring or any other equivalent resilient element, said resilient element 51 being suitable for being prestressed while the device is being opened. Advantageously, the movable support means 50 are displaceable between a first position (a non-dispensing position) and a second position (a dispensing position) that is the position for opening the reservoir. The movement between the first and second positions advantageously takes place along a curve. With reference more particularly to the embodiment shown in FIGS. 1 to 8, it should be observed that the movable support element 50 is made integrally with a rod 50 that is hinged relative to said body 10. A guide wheel 30 that is fastened on said rod 50 receives and guides the blisters. Turning the guide wheel 30 causes the blister strip 20 to advance. In a particular angular position, a given reservoir 21 is always in position to be opened by the opening means 40, i.e. by the perforator and/or cutter means 41. Advantageously, rotary positioning means 300 for positioning said guide wheel 30 in turning can be provided for accurately determining the angular position of said guide wheel 30 after each turn. In an advantageous variant shown in FIGS. 37 and 38, the positioning means 300 can comprise a projection or finger 301 having an end that co-operates resiliently with notches 38 that are provided around said guide wheel 30. Advantageously, the notches 38 have a V-shaped profile that automatically guides said finger 301 towards the central position of the notch, thereby guaranteeing accurate angular positioning at each turn. The guide wheel 30 preferably forms the drive means for driving the strip. An additional wheel 38 could optionally be provided so as to help guide and/or drive the blister strip 20, as shown in FIG. 21. Said rod 50 can be connected to a second rod 55 in such a manner as to form a V, the point of the V being formed by the pivot axis of the rod(s). The second rod, that can be stationary or pivotable, can support the resilient element 51, such as a spring, that also co-operates with an active element 57. FIGS. 5a to 8b show an actuation cycle of the device. FIGS. 5a and 5b show the device in its closed, rest position. While the device is being opened (FIGS. 6a and 6b), the two cap-forming lateral portions 11 and 12 are moved apart by pivoting on the body 10 in order to open the device. The active element 57 is thus urged against the second rod 55 so as to compress, and therefore stress, the spring 51. In this position, the rod 50 supporting the guide wheel 30 cannot be displaced in pivoting, since it is held by appropriate blocking means 100 (not shown in the overall views, but visible in FIGS. 9 to 12). It is while the user is inhaling through the mouthpiece 15 (FIGS. 7a and 7b) that the blocking means 100 are unblocked, thereby causing said rod 50 and therefore said guide wheel 30 to pivot towards the opening means 40, and thereby causing a reservoir 21 to be opened by means of said perforator and/or cutter means 41. Since the guide wheel 30 is fastened on a rod 50 that pivots about a pivot axis, the reservoir 21 is displaced along a curve in this embodiment. During opening, the curve provides a particular advantage that is described in greater detail below.

Advantageously, abutment means 350 are provided for accurately determining the dispensing position of the guide wheel 30 after each inhalation. The abutment means can comprise a lug 350, as shown in FIGS. 35 and 36, that is adapted to co-operate, when in the dispensing position, with one or more corresponding plane surfaces of the guide wheel 30. Preferably, one plane surface is associated with each recess. In this embodiment, the abutment 350 contributes to correct rotary positioning of the guide wheel 30 when the perforator and/or cutter means penetrate into the reservoir. The abutment 350 therefore defines not only the depth to which said perforator and/or cutter means penetrate into the reservoir, but also their centering relative to the reservoir, so as to guarantee optimum expulsion of the powder and reproducibility of the dose taken on each actuation. The abutment means 350 can be associated with the above-mentioned rotary positioning means 300, in such a manner as to predetermine in accurate manner each position of the guide wheel, in the non-dispensing position, in the dispensing position, and also while the guide wheel 30 is being displaced between said positions. This makes it possible to avoid any risk of the device blocking in the event of said guide wheel being badly positioned.

In the embodiment shown, while the reservoir 21 is being displaced towards its opening position in order to be opened by the perforator and/or cutter means 41, the perforator and/or cutter means 41 are preferably stationary relative to the body. However, it is possible to envisage that the perforator and/or cutter means 41 could also move during the step of opening the reservoir 21. For example, the perforator and/or cutter means 41 could be displaced towards the reservoir 21 while the reservoir 21 is being displaced towards the perforator and/or cutter means 41. In another variant, it is also possible to envisage that the reservoir 21 and the perforator and/or cutter means 41 are displaced in the same direction during actuation, the reservoir 21 being displaced more quickly in said direction, such that it comes into contact with said perforator and/or cutter means 41 in order to be opened.

As explained above, it is desirable for the opening means to be actuated by the user inhaling. In order to trigger the reservoir opening means by inhalation, an inhalation trigger system is provided that advantageously comprises a unit 60 that is displaceable and/or deformable under the effect of inhalation, the unit 60 being adapted to release the blocking means 100. The unit 60 advantageously comprises a deformable air-chamber 61 that co-operates with the blocking means 100 of said movable support means 50. Inhalation by the user causes said deformable air-chamber 61 to deform, thereby making it possible to release said blocking means 100 and therefore unblock the movable support means 50, so as to make it possible to displace the guide wheel 30 and a respective reservoir 21 towards its opening position. Advantageously, the air chamber 61 can comprise a deformable membrane, such as a bellows or a pouch 62, that can be connected firstly to the mouthpiece 15, and secondly to said blocking means 100 in direct or indirect manner. Thus, during inhalation, the bellows or pouch 62 deforms and contracts, causing said blocking means 100 to be displaced into an unblocking position. In a variant, the bellows could be replaced by any deformable membrane.

The inhaler further includes a dispenser chamber 70 for receiving the dose of powder after a respective reservoir 21 has been opened. The dispenser chamber 70 is advantageously provided with at least one bead 75 that is displaced inside said chamber 70 during inhalation so as to improve dispensing of the air and powder mixture after a reservoir 21 has been opened, in order to increase the effectiveness of the device.

In a particular variant, the deformable air-chamber 61 co-operates with the dispenser chamber 70. The dispenser chamber 70 can therefore be connected to the reservoir-opening means 40, and in particular to the perforator and/or cutter means 41, and can include a dispenser orifice 79. The dispenser chamber 70 can itself optionally be displaceable between a rest position and an inhalation position, such that when a user inhales through the mouthpiece 15, causing the deformable air-chamber 61 to deform, the dispenser chamber 70 is displaced from its rest position to its inhalation position. In the inhalation position, the dispenser orifice 79 comes to be placed in said mouthpiece 15, so as to guarantee good dispensing of the dose, as shown in FIG. 7*b*. In the embodiment shown in FIGS. 2*a*, 2*b*, 5*b* to 8*b*, 26, and 27, the bellows 62 is therefore connected firstly to the mouthpiece 15, and secondly to the dispenser chamber 70, in the inhalation flowpath of the user. As shown in the drawings, it can be advantageous for the opening means 40, in particular for the perforator and/or cutter means 41, to be formed directly on said dispenser chamber 70, e.g. at the end of a channel 69 leading to said chamber 70. Similarly, in its inhalation position, the dispenser chamber 70 can be adapted to release the blocking means 100, which were previously holding the movable support means 50 in the initial position, so as to enable the movable support means 50 to displace the reservoir 21 towards the opening position.

After inhalation, as shown in FIGS. 8*a* and 8*b*, when the user closes the device, all of the components return to their initial, rest position, i.e. the movable support means 50 pivot about their pivot axis 56 to return to their initial or first position by moving away from the reservoir opening means 40, and the active element 57 that co-operates with the prestressed spring 51 is also returned to its initial rest position in which the spring 51 is not compressed. The device is thus ready for a new utilization cycle.

In a variant, other inhalation trigger means could also be used, e.g. using a pivotable valve flap that, while the user is inhaling, pivots under the effect of the suction created by the inhalation, with pivoting of the valve flap causing the blocking means blocking the movable support means to be released, thereby causing the reservoir to be displaced towards the opening means.

Figure 3:
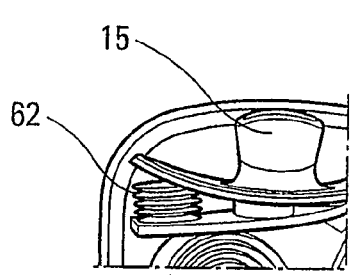
FIG. 3 is a diagrammatic view of another embodiment of the inhalation trigger system.

FIG. 3 shows a variant embodiment of the bellows 62, in which the bellows is not disposed directly between the mouthpiece 15 and the dispenser chamber 70, but is housed in the main body 10 below the dispenser chamber 70. In this variant embodiment, during inhalation, the bellows could even deform in order to expand, thereby causing the dispenser chamber to be displaced towards its inhalation position, whereas, in the above-described embodiment, the bellows contracts during inhalation so as to pull the dispenser chamber towards its inhalation position.

Figure 4:
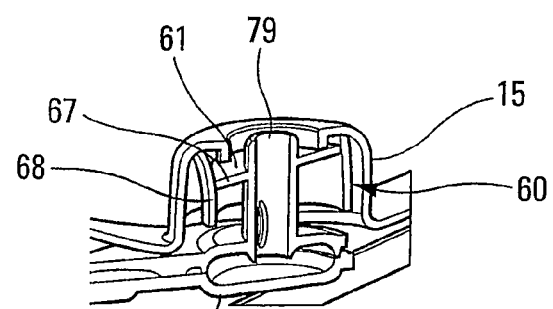
FIG. 4 is a diagrammatic view of still another embodiment of the inhalation trigger system.

FIG. 4 shows another embodiment in which the bellows (or the membrane) is replaced by a piston 67 or the like, sliding in a hollow sleeve 68 so as to deform the air chamber 61. The piston 67, which can be made in the form of a thin plate, can include a hole (not shown) for controlling resistance to the flow of air. In the embodiment shown, the piston 67 is secured to the dispenser chamber 70, and the sleeve 68 is secured to the mouthpiece 15, but the opposite could also be envisaged.

FIGS. 33 and 34 show another variant embodiment in which a pouch or a diaphragm 62 forms the air chamber 61. The pouch 62 is connected to the mouthpiece 15 via a channel 151 that is advantageously disposed around an expulsion channel 152 that is connected to the dispenser chamber 70. The pouch 62 is fastened to a rod that is connected to the blocking means 100, inhalation causing the pouch 62 to deform and therefore deforming the rod in order to displace said blocking means 100. FIGS. 39 and 40 show a variant embodiment of the pouch 62. Said pouch, advantageously made of silicone, can include a hem 620 that is adapted to seal with the body 10, e.g. between the body 10 and the mouthpiece 15. To do this, the hem 620 can be extended by a flange 625, also made of silicone, that becomes compressed by a snap-fastener portion 1001 of the body 10 in order to achieve sealing, and in particular to avoid any head loss in the inhalation flow.

FIG. 41 shows a detail of how the portion forming the mouthpiece 15 is fastened on the body 10, in a particular embodiment. The mouthpiece 15 can include a window 1500 that co-operates with a sloping projection 1010 of the body 10. Since a top portion 1011 of the body 10 is also jammed by a shoulder 1501 of the mouthpiece 15, the sloping projection 1010 guarantees sealing of the snap-fastening.

FIG. 42 shows a variant embodiment in which the pivot rod 50 that supports the guide wheel 30 includes an extension 501 which, in the inhalation position, comes to close substantially a hole 1550 provided in the mouthpiece 15. Thus, the inhalation flow, which prior to the guide wheel 30 and its rod 50 being displaced passes in part through the hole 1550, is mainly channeled towards emptying of said covered reservoir after said elements have been displaced and the hole 1550 has been closed, and therefore after the reservoir has been opened. This improves effectiveness during inhalation and helps to ensure that the reservoir is emptied in optimum manner.

In another advantageous aspect of the inhaler, the individual reservoirs or blisters 21 are formed on an elongate strip 20 that is stored in the form of a roll inside the body 10 of the device. Advantageously, the rolled-up blister strip 20 is held by inner walls of said body 10 without its "rear" end (rear in the displacement direction of the blister strip 20) being fastened relative to said body 10, thereby enabling the blister-strip roll to be assembled more easily inside the device. The blister strip 20 is displaced by the user, advantageously by means of the guide wheel 30 that advantageously presents at least one and preferably more recesses 31 having a shape that corresponds to the shape of the blisters. Thus, when the guide wheel 30 turns, it drives the blister strip 20. No other drive system is necessary for displacing the blisters 21 during each actuation. Naturally, in a variant or in additional manner, it is possible to use other means for advancing the blister strip, e.g. providing a profile on the longitudinal lateral edges of the blister strip, said profile being adapted to co-operate with appropriate drive means. In addition, holes formed along the lateral edges of the blister strip could also be used to cause the blister strip to advance by means of toothed wheels co-operating with said holes.

The blocking means 100 are for holding the movable support means 50 in their initial position, and for preventing the reservoir 21 from being displaced towards its opening position until the user inhales. The blocking means 100 must be able to be released in safe, reliable, and easy manner while the user is inhaling, so that the reservoir is displaced quickly and reliably towards the opening means, without any need for excessive force. In the embodiments shown in FIGS. 9 to 12, the blocking means 100 can comprise two elements 101, 102 that are connected together. The second element 102 is turned along arrow B when an appropriate inhalation threshold is reached, such turning of the second element 102 thus causing the first element 101 to be released, the first element 101 also being subjected to a force along arrow A from the movable support means 50, under the effect of the resilient element 51 that was prestressed while the device was being opened. The first element 101 could be pivotally mounted about a pivot point 109 disposed between its two ends, a first end being subjected to force from the movable support means 50 along arrow A, and the other end co-operating with the second element 102. In this embodiment, shown in FIGS. 9 and 10, when the second element 102 has turned along arrow B following inhalation, the end of the first element 101 that was blocked by the second element 102 is therefore displaced in a direction (arrow C) that is opposite to the force (arrow A). In a variant, shown in FIGS. 11 and 12, it is also possible to use a rotary rod or bar 102 that co-operates with a peg 101 that exerts an axial force (arrow A) on said rod 102 when the device is prestressed. The rotary bar 102 advantageously presents a shape that is suitable for enabling said stressed rod 101 to be displaced freely in the direction A of the force exerted on it by the prestressed movable support means 50 when said rotary bar 102 has turned through a certain angle. For example, as shown in FIG. 11, the rotary bar 102 includes a bottom portion 107 of diameter that is greater than a top portion 108, so that after turning through 90°, the shoulder 106 that is formed between the two portions 107 and 108 pushes the axial rod 101 in such a manner as to off-center it relative to the central pin of the rotary bar 102, so that the axial rod 101 slides along the rotary bar 102 and can move downwards in FIGS. 11 and 12 in the direction of arrow A, so as to enable the movable support means 50 to be displaced towards the reservoir-opening position. Other variant embodiments can obviously be envisaged in order to achieve blocking, and to release said blocking while the user is inhaling.

In still another aspect of the inhaler, dose counter or indicator means 120 are also provided. The means can either include numbers or symbols 125 that are marked directly on the blister strip 20, and that are visible through an appropriate window 19 in the body 10 of the device. In a variant, it is possible to envisage using a rotary disk 121 including numbers or symbols 125, e.g. marked in a spiral on the disk. In this event, a slidable element (not shown) with an appropriate window could be engaged in a spiral track that is provided on the disk 121, so as to display the number or symbol 125 that is pertinent to the current dose. Finally, indicators including rotary wheels, e.g. a units wheel and a tens wheel could also be envisaged. Other variants can also be envisaged, such as the use of two superposed rotary disks, or a single disk with the numbers marked around its periphery.

After opening one or more blisters, the blister-strip portion 35 with the empty reservoirs must be suitable for being stored in easy and compact manner in the device. Advantageously, the used blister strip 35 is rolled-up automatically, once again forming a roll. Advantageously, the end of the used blister strip 35 (the "front" end of the blister strip 20) can be fastened to a rotary shaft or element 150 that accompanies each displacement of the blister strip by turning through a corresponding angle. This encourages the used blister strip 35 to roll up. In advantageous manner, the shaft 150 does not apply any traction nor any other drive force on the blister strip 20, but serves only to exert rotary guidance on its end, in order to roll up the used portion 35 of the strip.

In another advantageous aspect of the inhaler, used-blister flattener means 160 can be used to flatten the blisters 21 once the dose that they contain has been emptied. This makes it possible to reduce the storage volume for the used blister strip 35. The flattener means 160 could be constituted by two cylinders between which the used blister strip 35 passes. The cylinders 160 could be smooth or they could present an appropriate profile (e.g. fluted as shown in FIG. 25) on their peripheral surface so as to provide optimum effectiveness, while requiring minimum force in order to flatten used or empty blisters.

Figure 16:
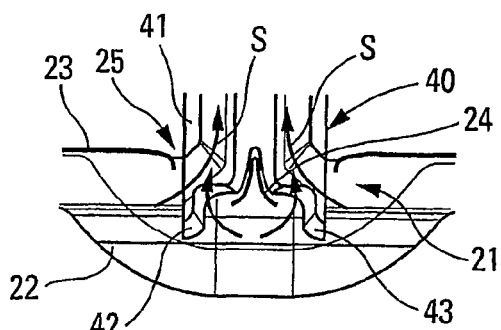

In still another aspect of the inhaler, the opening means 40 for opening the reservoirs 21 comprise perforator and/or cutter means 41. The perforator and/or cutter means 41 preferably have an appropriate shape, such that the cut wall portions 24 of the blister 21 fold towards the inside of the blister without covering the openings 25 formed by the perforator and/or cutter means 41. FIGS. 13 to 16 show a cycle of opening and expelling the dose of a blister. Advantageously, the perforator and/or cutter means 41 include at least two opposite perforating ends 42, 43 that are separated from each other by an appropriate distance 44. The perforator and/or cutter means 41 advantageously create a central fold in the cut wall portions 24, making it possible for the openings 25 that are formed not to be covered at all by any cut wall portion 24. Advantageously, as shown in FIGS. 13 to 17, each perforator end 42, 43 is dish-shaped and is formed by a hollow cylindrical portion that is cut out in part and that has sharp edges. Advantageously, the incoming air (arrow E) penetrates into the open blister 21 over the outside of said perforator and/or cutter means 41, as shown in FIG. 5. By way of example, this can be obtained as a result of the movable support means 50 being displaced towards the reservoir-opening position along a curved line. The displacement along a curve results in one or more openings 25 that are slightly larger than the dimensions of the perforator and/or cutter element 41. Therefore, this enables the inhalation air to flow over the outside of said perforator and/or cutter element 41 in order to penetrate into the blister 21. If necessary, special means could also be provided for forming an opening outside said perforator and/or cutter element 41, e.g. ribs 410 or any other appropriate external profile on said perforator and/or cutter element 41 (see FIGS. 29 to 32). The flow of outgoing air carrying powder (arrow 5) preferably leaves the reservoir or blister 21 via the hollow inside of said perforator and/or cutter means 41, as shown in FIG. 16. Optionally, as shown in FIG. 18, both the flow of incoming air (arrow E) and the flow of outgoing air carrying the powder (arrow S) could pass through respective hollow channels provided inside the perforator and/or cutter means 41. The special shape of the perforator and/or cutter element 41 as shown in the figures provides a "louvre" type cut that provides all of the advantages mentioned above, and in particular avoids the holes 25, that are created by perforating, from being covered, even in part, by perforated wall portions 24. This makes it possible to guarantee that the blister 21 is emptied as completely as possible, and therefore ensures that the dispenser is as effective as possible. In addition, metering reproducibility is optimum, with the same quantity of powder being expelled each time by means of the device of the invention.

FIGS. 29 and 30 show a variant embodiment of the perforator and/or cutter element 41, in which a central point 420 divides the outside of the element into a plurality of channels, in this example four channels. External splines 410 are provided on the outside edge so as to create lateral openings enabling the inhalation flow to enter into the reservoir.

FIGS. 31 and 32 show another variant embodiment that is fairly similar to the embodiment in FIGS. 13 to 17, namely with two perforator ends 42, 43 that are separated by a distance 44 that is adapted to house at least part of the cut wall portion of the blister. In this embodiment, the openings are disposed back to back, unlike FIG. 17 in which they are face to face. External splines 410 are also advantageously provided on the outside edge.

FIG. 26 shows a second embodiment of the inhaler. This second embodiment differs from the first embodiment in FIGS. 1 to 8 mainly by the outside shape of the device, and by the different shape of the resilient means 51 that make it possible to prestress the device while it is being opened. In this second embodiment, the body 10 includes only one cap element 11 that is to be opened in order to stress the device. During opening, a spring blade 51 is deformed by said cap element 11 on opening, thereby providing the stress that is provided by the spring 51 in the above-described embodiment. Once again, the spring blade 51 urges the movable support means 50 towards the reservoir-opening position in which the reservoir 21 is displaced against the opening means 40, but suitable blocking means 100, such as the blocking means described above, or other blocking means, are provided so as to prevent this displacement until the user inhales. Inhalation by the user unblocks said blocking means 100, thereby making it possible, via the opening means 40, to open the reservoir 21 and to dispense automatically the dose contained therein, and thereby making it possible, via the dispenser chamber 70 provided upstream from the mouthpiece 15, to expel said dose into the user's lungs. The movable support means 50 can be made in the form of a part made of deformable plastics material, said part incorporating the spring blade 51, an urging element 50 co-operating with the guide wheel 30, and one or two extensions 52, 53 that are adapted to co-operate with the body 10 so as to make it possible to stress the spring blade 51. In the embodiment shown, a first extension 52 co-operates with a toothed wheel 200 that is suitable for forming an anti-return ratchet and a roll-up system for rolling up the used blister strip 35. A second extension 53 can co-operate with the dispenser chamber 70, or it can be connected in any way to the blocking means 100.

FIG. 27 shows another embodiment that differs from the embodiment in FIG. 26 mainly by the different shape of the resilient means 51 for prestressing the device while the device is being opened. The shape of the body 10 of the inhaler is also changed slightly, even if the difference is not so great compared to the first embodiment in FIGS. 1 to 8. The different shape of the resilient means 51 that make it possible to prestress the device while the cap 11 is being opened, differs slightly from the shape shown in the second embodiment, but its function is strictly identical and is therefore not described in greater detail below. In this particular embodiment, the movable support means 50 are made integrally with a spring blade 51 that is deformed while the device is being opened, and an optionally-resilient second part 54 can be provided for rolling up the used blister strip 35, and/or for unblocking the blocking means 100. It should be observed that the blocking means 100 are not shown in FIGS. 26 and 27, and that they can be actuated in any appropriate manner.

FIG. 28 shows an external view of another advantageous embodiment of the inhaler that is fairly similar to the embodiment in FIGS. 1 to 8.

In all of the embodiments described above, the blister strip is formed by a strip presenting two ends. In a variant, it is possible to use a continuous strip. Other modifications are also possible without going beyond the ambit of the present invention.

The present invention therefore makes it possible to provide a dry-powder inhaler that performs the following functions:

a plurality of individual doses of powder stored in individual sealed reservoirs, e.g. 60 doses stored on a rolled-up strip;

the powder is released by perforation that is achieved by the user inhaling, the blister being perforated by means of an inhalation detector system that is coupled to a pre-stressed release system;

appropriately-shaped drive means that are engaged with blisters so as to displace the blister strip on each actuation, and to bring a new reservoir into a position in which it is to be opened by appropriate opening means; and a dose indicator that is mechanically connected to the movement of the blister strip.

Other functions are also provided by the device of the invention as described above. It should be observed that the various functions, even if they are shown as being provided simultaneously on the various embodiments of the inhaler, could be implemented separately. In particular, the inhalation trigger mechanism could be used regardless of the type of reservoir opening means, regardless of the use of a dose indicator, regardless of the way in which the individual reservoirs are arranged relative to one another, etc. The prestressing means and the inhalation trigger system could be made in some other way. The same applies for other component parts of the device.

The inhaler of the invention, incorporating all or some of the above-described functions, provides performance that is superior to the performance of existing devices. In particular, the inhaler of the invention provides a reservoir emptying factor of at least 90% on each actuation. The emptying factor, corresponding to the percentage of fluid that is expelled from an open reservoir while the device is being actuated, is advantageously greater than 95%, preferably even greater than 97%. In particular, this high emptying factor is even greater than the performance obtained with active inhalers that are generally more effective than passive inhalers, and in which it is not the inhalation flow that empties the blister and expels the dose but a flow of compressed air that is released while inhaling. The high emptying factor guarantees that the device of the invention is as effective as possible. Coupled with the inhalation-triggered opening, the high emptying factor guarantees that the fluid, specifically the powder, is dispensed in optimum manner into the user's lungs. The table below shows measurements taken with a budesonide/lactose mixture at 1.17% by weight, with various flow rates corresponding to typical inhalation flow rates. Thus, three measurements were taken with respective flow rates of about 7.5 liters per minute (L/min), 10 L/min, and 15 L/min. The measurements consisted in measuring the quantity of powder remaining in the blister after being emptied by the flow of air, and, by comparison with the quantity of powder inserted into the blister, thus measuring the emptying factor of said blister. The measurements show the very high effectiveness of the device of the invention, the emptying factor in this example being systematically at least equal to 97%.

| Flowrate (L/min) | Powder inserted into blister (mg) | Powder remaining in blister (mg) | Quantity of powder dispensed from blister (mg) | % of dose dispensed | |
|---|---|---|---|---|---|
| 7.5 | 10.63 | 0.00 | 10.63 | 1.00 | 0.98 |
| 7.5 | 10.18 | 0.13 | 10.05 | 0.99 | |
| 7.4 | 9.78 | 0.32 | 9.46 | 0.97 | |
| 10.0 | 9.86 | 0.31 | 9.55 | 0.97 | 0.99 |
| 10.0 | 10.38 | 0.00 | 10.38 | 1.00 | |
| 9.9 | 9.77 | 0.00 | 9.77 | 1.00 | |
| 15.0 | 10.01 | 0.00 | 10.01 | 1.00 | 1.00 |
| 14.5 | 9.76 | 0.04 | 9.72 | 1.00 | |
| 14.5 | 10.04 | 0.02 | 10.02 | 1.00 | |

The invention also provides improved emptying regularity of the reservoirs during successive actuations. Thus, for ten reservoirs of a blister strip, for example, it turns out that the emptying factor varies by less than 15%, advantageously less than 10%, preferably less than 5% from one reservoir to another. This improved regularity guarantees improved dose reproducibility, and therefore also improved effectiveness of the device of the invention.

Various modifications can also be envisaged by a person skilled in the art, without going beyond the ambit of the present invention, as defined by the accompanying claims.

The invention claimed is:

1. A fluid dispenser device including at least one individual reservoir (21) containing a single dose of fluid, such as powder, opening means (40) being provided for opening an individual reservoir (21) each time the device is actuated, the device being characterized in that the reservoirs (21) are made in the form of an elongate strip (20) comprising a plurality of individual reservoirs (21) disposed one behind another, said opening means (40) comprising perforator and/or cutter means (41) and movable support means (50), said movable support means (50) being adapted to displace an individual reservoir (21) against said perforator and/or cutter means (41) on each actuation, said displacement being performed automatically by the user inhaling.

2. A device according to claim 1, in which said movable support means (50) are displaceable between a non-dispensing position and a dispensing position, said movable support means (50) being urged towards their dispensing position by resilient means (51), such as a spring or a spring blade, and being held in their non-dispensing position by blocking means (100).

3. A device according to claim 2, in which said blocking means (100) are released by the user inhaling.

4. A device according to claim 2, in which said resilient means (51) are deformable between a rest position, in which they do not urge the movable support means (50) towards their dispensing position, and a stressed position, in which they urge said movable support means (50) towards their dispensing position, said resilient means (51) being deformed manually into their stressed position before the user inhales.

5. A device according to claim 4, in which said device comprises a body (10) and a cap (11; 11, 12) that is movable between a closed position and an open position, opening the cap (11; 11, 12) deforming the resilient means (51) into their stressed position.

6. A device according to claim 2, in which the movable support means (50) are displaced in a curve between the non-dispensing and dispensing positions.

7. A device according to claim 2, in which said blocking means (100) comprise a first element that is movable between a non-actuated position and an actuated position, said first element (101) being secured to said movable support means (50), and a second element (102) that is movable between a blocking position and an unblocking position, said second element being displaced towards its unblocking position while the user is inhaling.

8. A device according to claim 7, in which said second element (102) is displaceable in turning.

9. A device according to claim 7, in which said second element (102) co-operates with a displaceable and/or deformable unit (60) that is adapted to be displaced and/or deformed during inhalation.

10. A device according to claim 9, in which said displaceable and/or deformable unit (60) comprises a deformable air-chamber (61) that is connected to an inhaler endpiece (15).

11. A device according to claim 10, in which said deformable air-chamber (61) comprises a deformable membrane, such as a bellows (62).

12. A device according to claim 11, in which said chamber (62) contracts during inhalation, causing the second element (102) of said blocking means (100) to be displaced towards its unblocking position.

13. A device according to claim 1, in which a dispenser chamber (70) is provided for receiving the dose of fluid contained in a reservoir (21) after said reservoir has been opened, said dispenser chamber (70) being connected firstly to said opening means (40), and secondly to a dispenser orifice (79) that is connected to an inhaler endpiece (15).

14. A device according to claim 13, in which said dispenser chamber (70) contains at least one movable bead (75).

15. A device according to claim 9, in which said dispenser chamber (70) is secured to said displaceable and/or deformable unit (60), such that said dispenser chamber (70) is displaced during inhalation.

16. A device according to claim 1, in which said opening means (40) do not move while the reservoir (21) is being opened.

17. A device according to claim 1, in which said opening means (40) move while the reservoir (21) is being opened.

18. A device according to claim 1, in which said movable support means (50) support a guide wheel (30).

19. A device according to claim 18, in which the guide wheel (30) includes at least one recess (31) that is adapted to receive and to guide a reservoir (21).

20. A device according to claim 19, in which said guide wheel (30) is firstly turnable about its central pin (39) so as to cause the elongate strip (20) to advance, and secondly displaceable, together with the movable support means (50), towards a dispensing position, so as to bring a reservoir (21) into contact with the reservoir opening means (40).

21. A device according to claim 20, in which the guide wheel (30) is turned manually by the user, whereas its displacement towards the dispensing position takes place automatically by the user inhaling.

22. A device according to claim 20, in which said guide wheel (30) co-operates with rotary positioning means (300) that are adapted to determine the rotary position of said guide wheel (30).

23. A device according to claim 22, in which said positioning means (300) comprise a projection or finger (301) that co-operates with notches (38) provided on the guide wheel (30).

24. A device according to claim 19, in which, in the dispensing position, the guide wheel (30) co-operates with abutment means (350) that are adapted to determine the dispensing position of said guide wheel (30) after inhalation.

25. A device according to claim 24, in which said abutment means (350) comprise a lug (350) that is adapted to co-operate with at least one plane surface of said guide wheel (30) in the dispensing position.

26. A device according to claim 1, in which said opening means (40) comprise perforator and/or cutter means (41) that are adapted to cut a closure wall (23) of the reservoir (21) in such a manner that the cut portion(s) (24) does/do not obstruct the opening(s) (25) that is/are formed.

27. A device according to claim 1, including a dose indicator (120) for indicating to the user the number of doses that have been dispensed or that remain to be dispensed.

* * * * *